(12) United States Patent
Lenzi-Brangi et al.

(10) Patent No.: US 7,056,497 B2
(45) Date of Patent: *Jun. 6, 2006

(54) HAIR BLEACH PRODUCT

(75) Inventors: Anne Marie Lenzi-Brangi, Orange, CT (US); Mary Larkin, So. Salem, NY (US); Stephen Casperson, Milford, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 32 days.

This patent is subject to a terminal disclaimer.

(21) Appl. No.: 10/108,664

(22) Filed: Mar. 28, 2002

(65) Prior Publication Data

US 2002/0179109 A1 Dec. 5, 2002

Related U.S. Application Data

(60) Provisional application No. 60/280,394, filed on Mar. 30, 2001.

(51) Int. Cl.
*A61K 7/135* (2006.01)
*A16K 7/06* (2006.01)

(52) U.S. Cl. ........................................ 424/62; 424/70.1

(58) Field of Classification Search ................. 424/62, 424/70.1, DIG. 3
See application file for complete search history.

(56) References Cited

U.S. PATENT DOCUMENTS

| | | | |
|---|---|---|---|
| 4,226,852 A | | 10/1980 | Tesmann et al. |
| 4,327,751 A | * | 5/1982 | Evans ........................ 132/208 |
| 4,507,278 A | | 3/1985 | DeMarco et al. |
| 4,834,767 A | | 5/1989 | Helioff et al. |
| 5,294,436 A | * | 3/1994 | Cope et al. .................... 424/62 |
| 5,575,989 A | | 11/1996 | Caskey |

FOREIGN PATENT DOCUMENTS

EP       FR2788975 A1  *  8/2000

* cited by examiner

*Primary Examiner*—Thurman K. Page
*Assistant Examiner*—Lakshmi Channavajjala
(74) *Attorney, Agent, or Firm*—Michael J. Sambrook; Brian M. Bolam; Tara M. Rosnell

(57) ABSTRACT

The present invention relates to a substantially ammonia free hair bleach product. Specifically, the invention concerns hair bleach products that comprise a hydrogen peroxide developer; a powder activator containing a mixed persulfate oxidizing system, and a monoethanolamine alkalizing agent.

19 Claims, No Drawings

000
HAIR BLEACH PRODUCT

This Application claim the benefit of Provisional Application No. 60/280,394, filed Mar. 30, 2001.

FIELD OF INVENTION

The present invention relates to a substantially ammonia free hair bleach product. Specifically, the invention concerns hair bleach products that comprise a peroxide-based developer; a powder activator containing a mixed persulfate oxidizing system, and a monoethanolamine alkalizing agent.

BACKGROUND OF THE INVENTION

Hair bleaching is a well known process in the hair cosmetic field. Hair bleaching involves the application of an oxidizing agent to the hair for a period of time effective to achieve a desired lighter hair shade. The oxidizing agent typically is a hydrogen peroxide solution in concentrations ranging from 6 to 12% by weight. The hydrogen peroxide is applied to the hair under alkaline pH conditions and gradually lightens the shade of the hair by oxidizing the melanin that gives it color. 28% Ammonium hydroxide is typically added to the peroxide solution at the time of use to provide the highly alkaline environment needed during use.

To enhance the lightening efficacy of the highly alkaline hydrogen peroxide solution, it is known to incorporate a persulfate salt as a "booster". The sodium, potassium or ammonium persulfate salt is provided as a powder, which is admixed with the hydrogen peroxide solution and the ammonium hydroxide solution. The mixed product is then applied to the hair for a period of time effective to achieve the desired lighter hair shade. Because of the incorporation of the persulfate and when used with a 10 to 40% by volume hydrogen peroxide solution activated by 28% ammonium hydroxide, substantial lightening of hair can be achieved. Such products, typically sold in kit form, are referred to in the industry as bleach blonding products.

The disadvantage of such products that utilize ammonium hydroxide to provide alkalinity is the significant release of ammonia, which imparts a highly unpleasant odor. The initial attempts by the inventors herein to formulate a three component hair bleach product of the type comprising a developer component; a powder activator component, and an aqueous based alkalizing agent component substantially free of ammonium hydroxide, but with sufficient oxidizing capacity to provide a bleach blonding product that lightens hair safely and rapidly, were at first unsuccessful. These attempts either (a) did not provide proper lightening of the hair, or (b) resulted in excessive foaming (also referred to a "creeping" or "puffing") when the components of the kit comprising an alkali metal persulfate powder activator, the hydrogen peroxide developer, and the monoethanolamine alkalizing agent were mixed together in an applicator container.

Accordingly, it is an object of the present invention to provide a hair bleach product substantially free of ammonium hydroxide.

It is a preferred object of the invention to provide a hair bleach product free of ammonium hydroxide.

A corollary object of the invention is to provide a hair bleach product that has little or no telltale ammonia odor during use.

It is another object of the invention to provide a hair bleach product in kit form comprising a non ammonia alkalizing agent composition, a hydrogen peroxide developer composition and a persulfate activator powder composition (as defined below) that has sufficient oxidizing capability to lighten hair to a blonde shade without excessive foaming.

SUMMARY OF THE INVENTION

The hair bleach product of the present invention is in kit form and comprises in separate packages within the kit a peroxide developer; a powder activator and an alkalizing agent composition.

The peroxide developer contains from about 6 to about 12% by weight hydrogen peroxide (corresponding to a 20 to 40 volume solution), which is an oxidizing agent capable of lightening hair to some extent.

The powder activator contains a mixture of (i) an alkali metal persulfate selected from the group consisting of sodium persulfate and potassium persulfate, and (ii) ammonium persulfate. The activator powder contains from about 40 to about 80% by weight total persulfate, the weight ratio of the alkali metal persulfate (i) to the ammonium persulfate (ii) being from about 3:1 to about 1:2. Potassium persulfate is the preferred alkali metal persulfate.

The alkalizing agent component composition preferably has a thickened liquid, gel, cream or other substantially nonflowing rheology and contains from about 10 to about 25% by weight monoethanolamine. The alkalizing agent composition is substantially free of an ammonia based alkalizing agent.

DETAILED DESCRIPTION OF THE INVENTION

The hair bleach product of the present invention is formulated substantially without ammonium hydroxide. The hair bleach product is further adapted to provide sufficient lightening within a given period of time so that hair may be bleached to a blonde shade. The product is further formulated to ensure that excessive foaming does not occur when the components comprising the hair bleach product are combined. The hair bleach product of the present invention comprises (a) a peroxide solution, generally referred to in the field as the developer component; (b) a powder activator component, also referred to in the field as a lightening powder or a booster, and (c) an alkalizing agent component.

These three components (a), (b) and (c) are typically provided in the form of a kit, which further includes instructions for use, and which optionally may contain a hair pretreatment component or a hair post treatment component. The three essential components (a), (b) and (c) of the hair bleach product kit are admixed at the time of use in an applicator device that is preferably part of the kit, typically a container for one of the three components (a), (b) or (c).

The hair bleach product is substantially free of ammonium hydroxide or other ammonia based alkalizing agent used in the commercially available prior art products. Accordingly, the hair bleach product of the present invention is referred to herein as substantially ammonia free, which means that the level of the ammonia based alkalizing agent such as ammonium hydroxide is sufficiently low as to avoid a hair bleach product that exhibits a telltale ammonia odor offensively noticeable to the consumer during application of the hair bleach product to the hair. Criteria in determining whether a hair bleach product is substantially ammonia free is set forth below in the section describing the alkalizing agent component composition (c). Most preferably, however, the alkalizing agent component of the present invention does not contain ammonium hydroxide or other ammonia based oxidizing agent. The ammonium persulfate present in the powder activator component is not considered an ammonia based alkalizing agent in accordance with the present invention because its incorporation does not, at the levels in which it is present in the bleach product applied to the hair and following mixing of the three essential components, result in release of ammonia in noticeable levels.

The Developer Component

The developer component composition comprises a hydrogen peroxide solution. The solution contains from about 6 to about 12% by weight hydrogen peroxide. (This corresponds to a 20 to 40 volume solution, and is referred to as, e.g., 20 volume, 30 volume or 40 volume hydrogen peroxide. This concentration unit refers to the amount of oxygen released from one volume of the hydrogen peroxide solution. Thus, one volume of a 30 volume peroxide solution is able to liberate 30 volumes of oxygen.)

The developer component composition preferably contains additional ingredients to facilitate its use and performance. Thus, the developer component composition further contains one or more of the following adjuvants: a thickener, an emulsifier, or a hair conditioning agent. Each of these constituents is present in the developer component in sufficient amount to provide its intended function in the developer component composition or in the final product mixture when the developer component is mixed with the activator powder component and the alkalizing agent component. Suitable adjuvants are those that are stable to hydrogen peroxide. Suitable thickeners are, for example, cetearyl alcohol and stearamidopropyl dimethylamine. Nonionic polymeric thickeners, in particular polyether urethanes sold under the tradename Aculyn by Rohm & Haas Company, especially Aculyn 44 and 46, are suitable. Anionic acrylate polymers, e.g., such polymers sold under the tradename Aculyn, e.g., Aculyn 22, 28 and 33, by Rohm and Haas may be used. Other useful thickeners are identified in International Cosmetic Ingredient Dictionary and Handbook, v. 2, pages 1810–1812 ($8^{th}$ Edition 2000) (CFTA) incorporated by reference herein, although stability in the presence of hydrogen peroxide would have to be confirmed with the manufacturers. Generally, the thickening agents are present in an amount effective to provide a viscosity of from 3,000 to about 40,000 cps, preferably 5,000 to about 30,000 cps. Typically, the thickener is present in an amount ranging from about 0.05% to about 5%, preferably about 0.1 to about 2.5%, depending on the choice of thickener agent and the degree of thickening that is desired.

The emulsifiers present in the developer component are typically in the range of from about 0.05 to about 10% preferably from about 0.1 to about 5%, especially 0.5 to 2.5% by weight of the developer composition. Suitable emulsifiers are glyceryl stearate, oleth 2, oleth-10, PEG-75 lanolin and ceteareth-20. Often, mixtures of emulsifiers are employed. The emulsifiers, which are surface active agents, may also contribute to thickening of the composition. Other emulsifiers are identified in the above-cited CTFA Ingredient Dictionary and Handbook, v. 2, at pages 1795–1803. Compatability with peroxide should be confirmed.

The developer composition may further contain an antifoam material such as simethicone in low concentration, to prevent foaming during manufacture, an acidifying material, a preservative, etc. while conventional hair conditioning agents may be incorporated in the developer if compatible at the acidic conditions and in the presence of hydrogen peroxide. Conditioning agents are generally incorporated in the alkalizer component.

The pH of the developer component is generally in the range of from about 2.5 to about 5.5, especially about 3.0 to about 4.

The Powder Activator Component

The powder activator component of the present invention comprises a mixture of an alkali metal persulfate and ammonium persulfate. We have found that the use of the mixture of these persulfates, when combined with the developer component of the present invention and the nonammonia alkalizing agent component of the present invention substantially reduces the tendency of the mixture to foam. This is particularly important when the product components are admixed in an applicator device that is provided with the kit. Thus, the mixed persulfate system prevents the foam from filling and possibly overflowing the applicator provided with the kit. In addition the product is more suitable for dispensing when excess foaming has not occurred because waiting for the foam to subside is unnecessary.

The powder activator component contains from about 40 to about 80%, preferably 50 to 70%, of the persulfate mixture by weight of the activator component composition. It has been found that the weight ratio of the alkali metal persulfate to the ammonium persulfate is from about 3:1 to about 0.5:1, preferably about 2.25:1 to about 1.5:1, most preferably about 2:1. The preferred alkali metal persulfate is potassium persulfate. Sodium persulfate may also be used. Other alkali metal persulfates are not recommended as the alkali metal persulfate in view of cost, activity, etc.

The powder activator component further contains an alkalinity agent to ensure an alkaline bleach product when the product components are mixed. Suitably, the alkalinity agent is sodium silicate present in the activation powder component in an amount of from about 20 to about 50% by weight of the powder activator component composition, preferably from about 30 to 40% by weight.

In another embodiment the powder activator component may contain a colorant selected from the group consisting of water insoluble pigments or lakes (and mixtures thereof (hereinafter "pigment"), generally in an amount of up to about 2.5% by weight of the powder activator component, preferably from about 0.1 to about 2% by weight. The pigment should be compatible with the other ingredients in the hair bleach product, and in particular it should be compatible with hydrogen peroxide. The pigment imparts to the hair bleach product a color that is visible when the product is applied to the hair, and thus imparts a visual cue to the hair colorist as to where the product has been applied. Suitable pigments include ultramarine blue, D&C yellow No. 10 aluminum lake, chromium oxide green, D&C Red No. 30 lake, and D&C yellow No. 5 zirconium lake. Although the incorporation of the pigment in the powder activator component is preferred, this adjuvant may also be incorporated in the alkalizer component or in the developer component, provided there is compatibility with the constituents of those other components.

A dessicant such as silica is also typically incorporated to prevent moisture from prematurely reacting with the presulfates. The silica is a positive amount generally less than about 5% by weight, usually from about 0.1% to about 3% by weight of the activator component. A lubricant may be incorporated to assist in dry blending of the powder materials, for example, a surfactant such as sodium lauryl sulfate may be incorporated in an amount of up to about 3% by weight of the composition. Each of the adjuvant constituents is present in the powder activator component in sufficient amount to provide its intended function in the powder activator component composition or in the final product mixture when mixed with the developer and the alkalizing agent.

The Alkalizing Agent Component

The third essential component is the alkalizing agent component, which contains in an aqueous vehicle monoethanolamine as the alkalizing agent. The alkalizing agent component is substantially free of an ammonia based alkalizing agent as previously stated.

This component composition generally has a pH of from about 10 to 12, preferably from about 10.5 to 11.5, especially about 11, by incorporating an effective amount of the monoethanolamine to achieve such pH values. Generally, the monoethanolamine is present in an amount of from about 10 to about 25% by weight of the alkalizing agent component, preferably about 12 to about 21% by weight.

Preferably, the alkalizing agent component is in the form of a thickened liquid, a gel or a cream, which form facilitates its admixture with the developer and activator powder components, although aqueous solutions, e.g., thin lotions, can be used.

The adjuvants useful in achieving the desired form of the alkalizing agent component and their incorporation to form the gel, the cream or the thickened liquid are well known to those of ordinary skill in the art. Such useful adjuvants are thickeners, surface active agents, and emulsifiers, all as described above in the section on the developer component. Also useful as adjuvants are fragrances, colorants, herbal extracts, and the like.

A gel composition is obtainable using oleic acid as a gelling agent and may further include a blend of anionic and nonionic surface active agents. Suitably, the oleic acid gelling agent is present in an amount of from about 0.1 to about 10% by weight of the alkalizing agent component. The surface active agents are typically present in an amount of from about 0.1 to about 15% by weight.

A cream composition having a viscosity of from about 50,000 to about 700,000 cps, preferably from about 100,000 to about 500,000 cps, can be obtained with a suitable amount of a surfactant thickening system. Useful surfactants are stearamide MEA, cocamide MEA, cetyl alcohol, myristyl alcohol, cetearyl alcohol, behenamidopropyl betaine, and stearamidopropyl betaine. Other thickening agents include the previously mentioned polyether urethane and polyacrylic acid-based polymers.

Conditioning agents may also be incorporated in amounts of from 0.1 to about 10%, preferably 0.5 to 5% by weight of the alkalizing component composition. Suitable conditioners are identified in the CTFA Ingredient Dictionary and Handbook referred to above at v. 2, pages 1752–1759 incorporated by reference, in particular betaines, such as cocamideopropyl betaine, and linoleamido propyl dimethyl amine dimer dilinoleate. Also useful is Polyquaternium 47, sold as Merquat 2001 by Nalco, Inc.

Generally, the concentration of an ammonia based alkalizing agent in the alkalizing agent component is less than 2% by weight, preferably less than 1% by weight, and especially less than 0.5% by weight. Most preferably, the ammonia based alkalizing agent is not present in the alkalizing composition. When higher concentrations of the ammonium persulfate are incorporated in the hair bleach product, the concentration of the ammonia based alkalizing agent should be kept at a minimum or excluded.

The Kit

The kit comprises premeasured amounts of the developer component, the powder activator component and the alkalizing agent component, along with instructions for use, an applicator tip for connection to the developer container, and gloves.

The developer component is preferably provided in a container which also serves as the container for mixing the components, and with applicator tip installed is used to apply the bleach product to the hair. The developer component container has sufficient head space to allow for the mixing of the other components.

The activator powder component is contained in a foil pouch packet, the entire contents of which are emptied by the consumer into the developer component container.

Lastly, the alkalizing agent component, which preferably is in gel form and contained in a tube, is added to the developer container applicator container. The addition of the alkalizing agent may cause minimal frothing to occur, but considerably less than the degree of foaming that was observed when the ammonium persulfate was not incorporated in the powder activator component.

The bleach composition applied to the hair (i.e., the mixture of the three components) has a viscosity of from about 20,000 to about 60,000 cps, preferably from about 30,000 to about 45,000 cps. The product remains on the hair until the desired lightening of the hair is achieved. Generally, this period of time is less than about 45 minutes.

The proportions of the three components used in the process are adapted so that there is no excess product or residual components of the product remaining after use. The proportions are predetermined so that the proper consistency of the product and the desired concentrations of the active ingredients as well as the adjuvants separately contained in one or more of the product component compositions are achieved on admixture of the three components, and so that the final product pH will be from about 10 to about 12, preferably from about 10.5 to about 11.5, especially about 11.

The final bleach product composition, based on mixing of the three essential component compositions comprises on an active ingredient basis:

|  | Range (wt./o) | Preferred Concentration (wt./o) |
| --- | --- | --- |
| Hydrogen Peroxide | 3.0–7.5 | 5.14 |
| Alkali Metal Persulfate | 3.0–8.0 | 5.67 |
| Ammonium Persulfate | 1.0–4.0 | 2.83 |
| Monoethanolamine | 2.5–7.5 | 5.12 |

The kit typically comprises from about 60 to about 220 ml. developer component; from about 14 to about 56 g. powder activator component; and from about 28 to about 112 g. alkalizing agent component. The kit generally comprises from about 3 to 5 parts developer component per part of activator powder component and from about 1.5 to about 2.5 parts alkalizing agent component per part of activator powder component. In a preferred embodiment 4 parts developer (112 g.), 1 part powder activator (28 g.) and 2 parts alkalizing agent component (56 g.) are mixed to provide the bleach composition applied to the hair. In this embodiment the developer contains about 30 volume hydrogen peroxide (about 9% by weight); the powder activator contains about 60% by weight of the mixed persulfates, with the ratio of the potassium persulfate to ammonium persulfate being about 2:1; and the alkalizing agent component contains about 18% by weight monoalkanolamine.

Generally, the final bleach product composition contains less than 0.5% of an ammonium based alkalizing agent, preferably less than 0.25%, and especially less than about 0.1% by weight.

Use of the Bleach Product

As described above the powder activator composition is added from its packet into the developer component, preferably in the applicator container, followed by addition of the alkalizing agent component. The contents are then mixed by shaking. Using the applicator tip, the final hair bleach product composition is applied to hair in conventional manner. The degree of lightening is checked periodically, and when the desired level of lightening is obtained, most usually in less than 45 minutes even for black hair, the product is rinsed from the hair, and the hair is preferably shampooed.

As previously described, it is preferred for the hair bleach product following admixture of the developer, powder activator and alkalizer components and as applied to the hair to contain a water insoluble pigment that imparts color to the product. This provides a visual cue to the hair colorist or to the consumer to indicate where the product has been applied on the hair. This is particularly important when substantially all the hair is to be bleached, i.e., where the colorist or consumer does not use a cap or foil that isolates discrete small portions of hair, as in highlighting and streaking techniques.

Following rinsing a hair conditioner, which may also be included in the kit, can be applied to the hair.

Product Manufacture

The hair bleach product of the present invention is made by conventional processes known in the art for making hair bleach products, and comprises admixing the ingredients of each of the component compositions in suitable vessels, followed by packaging in appropriate individual containers.

The present invention is further illustrated by the examples that follow. Unless otherwise indicated all percentages referred to herein are percent by weight on an active ingredient basis of the component compositions or of the mixed bleach product composition, as the case may be.

EXAMPLES

The composition of Examples 1 through 4 were prepared. Each comprised 4 parts of the developer component, 1 part of the powder activator component and 2 parts of the alkalizing agent component. Examples 1 and 2 are outside the scope of the invention; Examples 3 and 4 illustrate the invention.

The product of Example 1 is a conventional as it contains ammonium hydroxide as the alkalizing agent in the alkalizing agent component. A strong ammonia smell was readily noticed upon mixing of the components. The product of Example 2 contains only monoethanolamine as the alkalizing agent in the alkalizing agent component, but contains no ammonium persulfate. Substantial foaming occurred when the three components were mixed together.

The products of Examples 3 and 4 did not result in an appreciable ammonia odor, and produced little or no foam on mixing of the components. Hair treated with these products was substantially lightened in less than 45 minutes.

| Components | Example 1 Weight % | Example 2 Weight % | Example 3 (This Invention) Weight % | Example 4 (This Invention) Weight % |
|---|---|---|---|---|
| Developer Component | | | | |
| Hydrogen Peroxide (50% active) | 18.3 | 18.3 | 18.3 | 18.3 |
| Water | 73.85 | 73.85 | 73.85 | 73.849 |
| Glyceryl Stearate | 3.63 | 3.63 | 3.63 | 3.63 |
| Cetearyl Alcohol | 0.965 | 0.965 | 0.965 | 0.965 |
| Ceteareth-20 | 0.322 | 0.322 | 0.322 | 0.322 |
| PEG-75 Lanolin (50% wt active) | 0.74 | 0.74 | 0.74 | 0.74 |
| Wax | 0.73 | 0.73 | 0.73 | 0.73 |
| Stearamidopropyl Dimethylamine | 0.6 | 0.6 | 0.6 | 0.6 |
| Etidronic Acid (60% wt active) | 0.27 | 0.27 | 0.27 | 0.27 |
| Oleth-10 | 0.25 | 0.25 | 0.25 | 0.25 |
| Oleth-2 | 0.25 | 0.25 | 0.25 | 0.25 |
| Simethicone | 0.1 | 0.1 | 0.1 | 0.1 |
| | 100.0 | 100.0 | 100.0 | 100.0 |
| Activator Powder Component | | | | |
| Potassium Persulfate (98.4% wt active) | 55.65 | 55.65 | 39.7 | 61.5 |
| Sodium Persulfate (98.4% wt active) | 3.94 | 3.94 | | |
| Ammonium persulfate (98% wt active) | | | 19.8 | 21 |
| Silica | 2.7 | 2.7 | 2.75 | 1.6 |
| Sodium Lauryl Sulfate | 1 | 1 | 1 | 1.2 |
| Disodium EDTA | 1 | 1 | 1 | 1.2 |
| Sodium Silicate | 35.75 | 35.75 | 35.75 | 13.5 |
| | 100.0 | 100.0 | 100.0 | 100.0 |
| Alkalizing Agent Component | | | | |
| Water | 39.5 | 37.9 | 37.9 | 37.9 |
| Ethanolamine | 6 | 17.9 | 17.9 | 17.9 |
| Soytrimonium Chloride | 5.85 | 5.85 | 5.85 | 5.85 |

-continued

| Components | Example 1 Weight % | Example 2 Weight % | Example 3 (This Invention) Weight % | Example 4 (This Invention) Weight % |
|---|---|---|---|---|
| Propylene Glycol | 12.375 | 13.875 | 13.875 | 13.875 |
| Steareth-21 | 2 | 2 | 2 | 2 |
| Oleamide MIPA | 1 | 1 | 1 | 1 |
| Erythorbic Acid | 0.4 | 0.4 | 0.4 | 0.4 |
| Sodium sulfite | 0.1 | 0.1 | 0.1 | 0.1 |
| EDTA | 0.2 | 0.2 | 0.2 | 0.2 |
| C12-15 Pareth-3 | 5.4 | 5.4 | 5.4 | 5.4 |
| C11-15 Pareth-9 (90% wt active) | 0.7 | 0.7 | 0.7 | 0.7 |
| Oleic Acid | 4.365 | 4.365 | 4.365 | 4.365 |
| Ammonium Hydroxide (29% wt active) | 12 | | | |
| Botanical Extracts | 0.14 | 0.14 | 0.14 | 0.14 |
| Fragrance | 1.475 | 1.575 | 1.575 | 1.575 |
| Ethoxydiglycol | 2.915 | 2.915 | 2.915 | 2.915 |
| Cocamidopropyl Betaine (30% active) | 2.915 | 2.915 | 2.915 | 2.915 |
| PEG-150/Stearyl/SMDI Copolymer (19% wt active) | 2.665 | 2.665 | 2.665 | 2.665 |
| | 100 | 100 | 100 | 100 |

What is claimed is:

1. A hair bleach product in kit form comprising:
 (a) a peroxide-based developer component containing from about 6 to about 12% hydrogen peroxide by weight of the developer component;
 (b) a powder activator component comprising a mixture of (i) an alkali metal persulfate selected from the group consisting of sodium persulfate and potassium persulfate, and (ii) aminonium persulfate, the activator powder component containing from about 40 to about 80% total persulfate by weight of the activator powder component, the weight ratio of the alkali metal persulfate (i) to the ammonium persulfate (ii) being from about 3:1 to about 0.5:1, and
 (c) an alkalizing agent component comprising in an aqueous vehicle from about 10 to about 25% monocthanolaniine by weight of the alkalizing agent component, the hair bleach product being substantially free of an ammonia based alkalizing agent;
 wherein each of components (a), (b), and (c) are packaged separately;
 wherein the weight ratio of the developer component (a) to the powder activator component (b) is from about 3:1 to about 5:1; and
 wherein the weight ratio of the alkalizing agent component (c) to the powder activator component (b) is from about 1.5:1 to about 2.5:1.

2. The hair bleach product of claim 1 wherein the developer contains about 9% hydrogen peroxide.

3. The hair bleach product of claim 1 wherein the ratio of the alkali metal persulfate (i) to the ammonium persulfate (ii) in the powder activator component is from about 2.25:1 to about 1.5:1.

4. The hair bleach product of claim 3 wherein the powder activator component contains about 40% potassium persulfate and about 20% ammonium persulfate.

5. The hair bleach product of claim 1 wherein the alkalizing agent component contains from about 12 to about 21% monoethanolamine.

6. The hair bleach product of claim 1 wherein the alkalizing agent component contains about 18% monoethanolamine.

7. The hair bleach product of claim 1 wherein the developer component has a viscosity of from about 5,000 to about 30,000 cps.

8. The hair bleach product of claim 1 wherein the alkalizing agent component is in the form of a cream having a viscosity of from about 100,000 to about 500,000 cps.

9. The hair bleach product of claim 1 wherein the powder activator component further comprises a water insoluble colorant selected from the group consisting of pigments, lakes and mixtures thereof, said colorant being present in an amount effective to provide a visual indication of product application on the hair.

10. The product of claim 1 wherein the product, upon admixture of the components (a), (b) and (c) and as it is applied to the hair, contains on a weight basis: (i) from about 3 to about 7.5% hydrogen peroxide; (ii) from about 3 to about 8% by weight potassium persulfate; (iii) from about 1 to about 4% ammonium persulfate, and (iv) from about 2.5 to about 7.5% monoethanolamine.

11. The hair bleach product of claim 10 wherein the ratio of the alkali metal persulfate (i) to the ammonium persulfate (ii) in the powder activator component is from about 2.25:1 to about 1.5:1.

12. The hair bleach product of claim 11 wherein the powder activator component contains about 40% potassium persulface and about 20% ammonium persulfate.

13. The hair bleach product of claim 10 wherein the alkalizing agent component contains from about 12 to about 21% monoethanolamine.

14. The hair bleach product of claim 10 wherein the powder activator component further comprises a water insoluble colorant selected from the group consisting of pigments, lakes and mixtures thereof, said colorant being present in an amount effective to provide a visual indication of product application on the hair.

15. The hair bleach product of claim 14 wherein the colorant is selected from the group consisting of ultramarine blue. D&C Yellow No. 10 aluminum lake, chromium oxide green, D&C Red No. 30 lake, and D&C Yellow No. 5 zirconium lake.

16. The product of claim 10 wherein the developer component contains about 9% hydrogen peroxide; the powder activator component contains about 40% potassium persulface and about 20% ammonium persulfate, and the alkalizing agent component comprises about 18% monoethanolamine, the product containing on a weight basis 4 parts developer component, 1 part powder activator component and 2 parts alkalizing agent component.

17. A method of bleaching hair comprising mixing components (a), (b) and (c) of the hair bleach product of claim 1; applying the resulting mixture to hair for a period of time effective to lighten the hair, and removing the resulting mixture from the hair.

18. The method of claim 17 wherein the resulting mixture contains on a weight basis (i) from about 3 to about 7.5% hydrogen peroxide; (ii) from about 3 to about 8% by weight potassium persulfate; (iii) from about 1 to about 4% ammonium persulfate, and (iv) from about 2.5 to about 7.5% monoethanolamine.

19. The method of claim 18 wherein the developer component contains about 9% hydrogen peroxide; the powder activator component contains about 40% potassium persulfate and about 20% ammonium persulfate, and the alkalizing agent component comprises about 18% monoethanolamine.

\* \* \* \* \*